United States Patent [19]

Scattergood

[11] 4,237,033
[45] Dec. 2, 1980

[54] PRETREATMENT OF MICROCARRIERS FOR CELL CULTURE

[75] Inventor: Edgar M. Scattergood, Lansdale, Pa.

[73] Assignee: Merck & Co., Inc., Rahway, N.J.

[21] Appl. No.: 32,302

[22] Filed: Apr. 23, 1979

Related U.S. Application Data

[63] Continuation-in-part of Ser. No. 885,137, Mar. 10, 1978, abandoned.

[51] Int. Cl.³ .............................................. C08L 89/00
[52] U.S. Cl. .......................................... 260/6; 260/8; 435/284; 435/285
[58] Field of Search ............... 435/240, 241, 285, 284, 435/286, 287, 317; 260/6, 7, 7.5, 8

[56] References Cited

U.S. PATENT DOCUMENTS

| | | | |
|---|---|---|---|
| 3,717,551 | 2/1973 | Bizzini et al. | 435/241 |
| 3,850,748 | 11/1974 | Cook et al. | 435/241 |
| 3,910,819 | 10/1975 | Rembaum et al. | 435/240 |
| 4,036,693 | 7/1977 | Levine et al. | 435/284 X |

OTHER PUBLICATIONS

A. L. van Wezel, "Microcarrier Cultures of Animal Cells," *Tissue Culture Methods and Applications,* Academic Press, pp. 372–377; 1973.
David W. Levine et al., "Microcarrier Cell Culture: New Methods for Research-Scale Application'" Somatic Cell Genetics, vol. 3, No. 2 pp. 149–155; 1977.
R. E. Spier et al., "The Production of Foot and Mouth Disease Virus from BHK 21C 13 Cells Grown on the Surface of DEAE Sephadex A50 Beads," Biotechnology and Bioengineering, vol. 18, pp. 659–667; 1976.

*Primary Examiner*—Robert J. Warden
*Attorney, Agent, or Firm*—Donald J. Perrella; Julian S. Levitt

[57] ABSTRACT

A method is provided for pretreatment of microcarrier beads to make them suitable for use in mass culture of vertebrate anchorage dependent cells such as primary and diploid cells. The beads are soaked and heated in fetal calf serum (FCS) at from about 65° to about 95° C. for about 3 minutes to about 1 hour.

6 Claims, No Drawings

PRETREATMENT OF MICROCARRIERS FOR CELL CULTURE

RELATED APPLICATION

The present application is a continuation-in-part of copending application Ser. No. 885,137 filed Mar. 10, 1978 now abandoned.

RELATIONSHIP TO PRIOR ART

Microcarrier cultures of vertebrate anchorage dependent cells were first described by Van Wezel, Nature 216, 64 (1967). Anion exchange resin beads were used as the cell support in a stirred suspension culture. One suitable resin was DEAE-Sephadex A50, a polydextran matrix to which is bound diethylamino ethyl (DEAE) anion exchange groups. The chief difficulties of the technique are that there is a significant loss of cell inoculum and lack of reproducibility in stirred cultures. Bead toxicity or nutrient absorption have been ascribed as causes of these difficulties. These problems have been partially overcome by coating the beads, treating with a sequence of chemical/physical steps to reduce the charge (Levine et al., Somatic Cell Genetics, 3 No. 2, pp. 149–155, 1977), adding carboxymethyl cellulose or soaking the beads in bovine serum (Spier and Winterside, Biotech. and Bioengineering, 18 p. 659 (1976)).

EMBODIMENTS OF THE INVENTION

It has now been found that microcarrier beads can be pretreated to minimize inoculum loss and lack of reproducibility. This pretreatment involves soaking the beads in fetal calf serum and heating the beads in fetal calf serum for about 3 minutes to about 1 hour preferably from about 5 minutes to about 20 minutes, at about 65° to about 95° C. This pretreatment results in beads from which larger numbers of cells can be obtained in a shorter time period. Although we do not wish to be bound by theory, it is believed that the heating step causes the fetal calf serum proteins that are in proximity to the positive charges of the beads to denature, attach to the beads, and mask the excessively high charge.

Suitable microcarrier beads may be prepared from, for example, a matrix of crosslinked dextran (dextrans are high molecular weight polymers of D-glucopyranose synthesized from sucrose by a number of bacterial species), polyacrylamide, polystyrene, or styrene divinylbenzene copolymer lattice. The matrix preferably has anion exchange groups bound thereto. The anion exchange groups may be, for example, diethylaminoethyl or quaternary ammonium.

Specific examples of microcarrier beads are DEAE Sephadex A25, DEAE Sephadex A50, Sephadex G10, Sephadex G25, Sephadex G50, Amberlite IR45, Bio Rad AG-21K, and Cytodex TM 1.

Representative examples testing the untreated beads and the beads treated by the process of this invention are as follows:

Five variations using 75 cm² plastic Falcon flasks and two variations using 2-50 ml Bellco spinners were set up.

In both cases, 5 ml of sterile suspended DEAE-Sephadex A50 beads in phosphate buffered saline was added to 15 ml conical plastic centrifuge tubes. The concentration of beads was 1 gm dry weight per liter of final suspension. The saline was removed from each tube after the beads settled leaving 1.5 ml of bead volume to which 1.5 ml of fetal calf serum (FCS) was added and the tubes shaken. The bead/saline/FCS mixture in the tubes were then pretreated as shown in Table 1 below. The heat treatment was done in a beaker of water at the temperatures shown in Table 1 with occasional shaking. After settling, the solution above the bead bed volume was removed and medium 199 with 10% FCS was added to the 5 ml level. Forty milliliters of the same media (199 with 10% FCS) was added to the flasks or spinners, then the 5 ml of suspended beads, followed by 3 ml of a primary chick embryo cell suspension for the flasks and 2 ml of a embryo cell suspension for the spinners. The flasks and spinners were incubated at 37° C. The spinners were stirred at 60 RPM which kept the beads suspended. After 70 hours of incubation the cells were harvested by removing the media, washing with 20 ml of phosphate buffered saline, trypsinizing for ½ hour with 20 ml of KCl trypsin, adding 2 ml of FCS, whiffling, and counting the cells in a Coulter counter. The results are shown in Table 1 below. The higher cell yield of the FCS heat treated beads indicate that less inoculum loss occured. This is also confirmed by a count of the number of viable cells on the top surface of 10 random beads for each flask of Table 1. These results follow in Table 2.

TABLE 1

Representative Examples of Untreated and Treated Beads

| Flask No. | Pretreatment | Cell Yield × 10⁶ | Cells Out / Cells In | Percent Cell Increase |
|---|---|---|---|---|
| 1 | Soak in FCS | 27.5 | 0.94 | 0 |
| 2 | Soak in FCS + heat treat 10 min. at 75° C. | 43.1 | 1.47 | 57 |
| 3 | Soak in FCS + heat treat 10 min. at 80° C. | 44.6 | 1.52 | 62 |
| 4 | Soak in FCS + heat treat 10 min. at 85° C. | 44.0 | 1.50 | 60 |
| 5 | Soak in FCS + heat treat 10 min. at 90° C. | 45.1 | 1.54 | 64 |
| Spinner No. | | | | |
| 1 | Soak in FCS | 19.7 | 0.86 | 0 |
| 2 | Soak in FCS at 85° C. | 34.7 | 1.52 | 77 |

TABLE 2

Average Viable Cells on Top Surface of Beads at 24 Hours

| Flask No. | Cells/Bead |
|---|---|
| 1 | 1.3 |
| 2 | 9.1 |
| 3 | 9.6 |
| 4 | 9.0 |
| 5 | 6.7 |

In addition to the above data, this method has been scaled up to treat 80 g of beads at once.

To show the advantages of the pretreated beads of this invention, growth curves were obtained in 8 L. cultures comparing treated and untreated microcarriers present at the level of 1 gm. dry weight per liter of solution. The cultures were grown at 37° C. in medium 199 with 2% fetal calf serum added. Both cultures were inoculated with $4.7 \times 10^5$ cells/ml of primary chick embryo cells. At 70 hours, $9.2 \times 10^5$ cells/ml were available with the treated microcarriers versus $1.3 \times 10^5$ for the untreated.

We have also compared treated microcarriers with the reduced charge carriers described in the Levine et al., process, reference supra. Results are as follows:

The beads prepared by this invention method used 10 ml of a 10 gm dry weight per liter DEAE-Sephadex A50 bead solution, then permitted the beads to settle to obtain 2 ml of bead bed volume. A volume of 8 Ml. of saline were removed, and 3 ml fetal calf serum added, then the beads were heated at 80° C. for 10 minutes. The solution above the bead bed volume was then removed and medium 199 with 2% fetal calf serum was added to the 10 ml level.

The reduced charge beads were prepared using sufficient volume of reduced charge bead solution to obtain 2 ml of bead bed volume; the saline above the beads was removed, and medium 199 with 2% fetal calf serum was added to the 10 ml level.

Both beads were treated in 75 cm² plastic Falcon flasks like the previous examples using 40 ml media 199 with 2% FCS, 5 ml of bead solution, and 2.5 ml of a primary chick embryo cell suspension. The two flasks were harvested at 64 hours. Both beads showed high activity.

What is claimed is:

1. A process of treating microcarrier beads to enhance their suitability as a surface for cell culture which comprises soaking the beads in heated fetal calf serum prior to culturing cells on the beads.

2. A process according to claim 1 wherein the soaking is carried out for a period of from about 3 minutes to about 1 hour.

3. A process according to claim 2 wherein the soaking is carried out for a period of from about 5 minutes to about 20 minutes.

4. A process according to claim 1 wherein the heated fetal calf serum has a temperature of from about 65° to about 95° C.

5. A process according to claim 4 wherein the heated fetal calf serum has a temperature of from about 75° to about 90° C.

6. The beads prepared by the process of claim 1.